United States Patent [19]

McCombs et al.

[11] 4,272,444

[45] Jun. 9, 1981

[54] DEHYDROFORMYLATION OF STEROIDAL ALDEHYDES

[75] Inventors: Charles A. McCombs; Charles H. Foster, both of Kingsport, Tenn.

[73] Assignee: Eastman Kodak Company, Rochester, N.Y.

[21] Appl. No.: 178,043

[22] Filed: Aug. 14, 1980

[51] Int. Cl.³ .................................................. C07J 1/00
[52] U.S. Cl. .............................. 260/397.3; 260/397.2
[58] Field of Search ............................ 260/397.3, 397.2

[56] References Cited

U.S. PATENT DOCUMENTS

| | | | |
|---|---|---|---|
| 4,171,317 | 10/1979 | Krbechek | 260/397.3 |
| 4,226,785 | 10/1980 | Nelan | 260/397.25 |

*Primary Examiner*—Elbert L. Roberts
*Attorney, Agent, or Firm*—Clyde L. Tootle; Daniel B. Reece, III

[57] ABSTRACT

The invention relates to a process for dehydroformylation of dinorcholanaldehydes and dinorcholenaldehydes to form 17(20)-pregnenes or 20-pregnenes. The dehydroformylation is carried out using a noble metal catalyst, and preferably carried out in the presence of a hydrogen acceptor.

12 Claims, No Drawings

DEHYDROFORMYLATION OF STEROIDAL ALDEHYDES

The invention relates to a process for dehydroformylation of dinorcholanaldehydes and dinorcholenaldehydes to form 17(20)-pregnenes or 20-pregnenes. The dehydroformylation is carried out using a noble metal catalyst and preferably carried out in the presence of a hydrogen acceptor.

The catalytic removal of hydrogen and carbon monoxide is the reverse of the hydroformylation process, and for the purposes of the present invention, is termed dehydroformylation. The dehydroformylation of aldehydes is a new synthetic method in steroid chemistry, and only described in the literature for use in other chemical processes. For example, the literature reports that the decarbonylation of heptanal is carried out over a rhodium catalyst to obtain the expected hexane in a 86% yield, and a 14% yield of hexene, the product of dehydroformylation.

The catalytic splitting of isobutyraldehyde with the formation of propylene was observed by H. J. Hagemeyer, Jr. and G. C. DeCroes (Tennessee Eastman Company, 1954) using palladium and copper catalysts. Copper was found to have a very slight activity, and with palladium, the propylene was mostly hydrogenated to propane during the reaction. This dehydroformylation has been studied more recently by F. G. Gault (Bull. Soc. Chem. France, 1965, pp 1710-14) and J. Falbe (British Patent 1,241,646), who also found that palladium resulted in the production of propane by the reaction of propylene and hydrogen. However, the latter work does report a successful dehydroformylation with rhodium and platinum catalysts. Patents have also been issued on at least two processes for the hydroformylation of allyl acetate to the acetoxybutyraldehydes, and the dehydroformylation of the acetoxybutyraldehydes, or a part thereof, back to desired feedstock [U.S. Pat. No. 3,880,913 (1975) and U.S. Pat. No. 4,035,408 (1977)]. The hydrogenation and dehydroformylation of hydratropic aldehydes to styrenes has also been reported in the literature using nickel phthalocyanine [H. Kropt and J. Muller, *Liebigs Ann. Chem.*, 1236 (1976)]. However, it is recognized in the art that the conversion of dinorcholenic acid derivatives to 4,17(20)-pregnadien-3-ones or 4,20-pregnadien-3-ones has been difficult and only accomplished by reaction with lead tetraacetate and iodine, followed by elimination under basic conditions. This reaction is not desirable and other products are formed [B. Krieger and E. Kaspar, *Chem. Ber.*, 100(4), 1169 (1967)].

Other reported routes for the preparation of 17(20)-pregnenes or 20-pregnenes include the dehydration of 17- or 20-hydroxypregnanes and Wittig reactions on various 17-keto androstanes. However, the conversion of 3-ketodinor-4-cholen-22-aldehyde (an intermediate commercially available from soy sterols) to pregna-4,17(20)-dien-3-one or pregna-4,20-dien-3-one has not been reported in the literature. It would therefore be an advance in the state of the art to provide improved processes for the catalytic degradation of the side chain with preservation of a functionalized pregnene capable of being converted to androstenedione or the corticosteroids.

In accordance with the present invention, dinorcholanaldehydes and dinorcholenaldehydes can be dehydroformylated to the corresponding 17(20)-pregnenes or 20-pregnenes by heating the aldehyde with a noble metal catalyst at a temperature of at least 160° C., preferably carrying out the dehydroformylation in the presence of a hydrogen acceptor.

The dehydroformylation can be carried out over periods of time from about 1 to 4 hours, depending on the temperature of the reaction and catalyst employed. The temperature at which the dehydroformylation is carried out is from 160°-300° C., preferably 190°-260° C. At temperatures lower than 160° C., the rate of dehydroformylation is too slow for effective reaction. At temperatures greater than 300° C. decomposition with darkening of the steroid occurs. The rate of dehydroformylation proceeds quickly in the presence of hydrogen acceptors. The reaction actually proceeds faster in the absence of hydrogen acceptors, however, with decreased dehydroformylation and more saturated compounds formed. In fact, without a hydrogen acceptor, the saturated component is present in amounts up to 75% of the resulting material. The hydrogen acceptors include preferably benzalacetone but high yields of dehydroformylation have also resulted with cinnamaldehyde, mesityl oxide and various substituted chalcones (benzylideneacetophenones). The hydrogen acceptor preferably is an enone but need not contain an enone functional group, as dehydroformylation has also occurred with quinoline, ethylene, acetone, and hexachloroethane. Mixtures of hydrogen acceptors such as benzalacetone and quinoline can be used. The hydrogen acceptor is generally employed in an amount of from 0.5 to 3 equivalents, preferably about 1 to 1.5 equivalents, of hydrogen acceptor to the aldehyde to be dehydroformylated.

The catalyst preferably is a particulate palladium, platinum or rhodium material having a large surface area. Forms of such catalyst therefore can be, for example, palladium in the form of sponge, but the commonly supported forms of palladium work better. However, the rate of dehydroformylation is not the same with other catalysts as platinum and rhodium catalysts were much slower than palladium at similar temperatures. Moreover, the regioselectivity of the olefin product can mostly be controlled by proper choice of catalyst. The use of platinum on charcoal at temperatures of 190°-215° C. was not desired, and gave low yields of dehydroformylation. Palladium on charcoal or alumina with benzalacetone at 190°-215° C. produced exclusively the pregna-4,17(20)-dien-3-one as the olefin product. Some overoxidation at C-6 was observed. This could be partially avoided by the coaddition of quinoline. Furthermore, the use of palladium with quinoline, solely or in conjunction with benzalacetone, required temperatures of 245°-260° C. for reasonable conversion times. The formation of pregna-4,20-dien-3-one with a palladium catalyst has been observed at low conversion, and appears to be the kinetic product of the dehydroformylation of 3-ketodinor-4-cholen-22-aldehyde. The use of rhodium on charcoal or alumina with benzalacetone at 245°-260° C. produced pregna-4,20-dien-3-one in high yields. However, varying amounts of pregna-4,17(20)-dien-3-one are also formed and the extent of isomerization depends on time and temperature. The amount of catalyst employed varies with the steroidal aldehyde used and the speed of reaction desired for the dehydroformylation reaction. Generally, an amount of catalyst used can be equal to about 3 to 7 percent, preferably 5 percent, based on the weight of the steroidal aldehyde to be dehydroformylated.

This invention can be further illustrated by the following examples, although it will be understood that these examples are included merely for purposes of illustration and are not intended to limit the scope of the invention unless otherwise specifically indicated.

EXAMPLE 1

3-Ketodinor-4-cholen-22-aldehyde (2.0 g, 0.006 mole and benzalacetone (0.89 g, 0.006 mole) were mixed with 0.1 g of 5% palladium on charcoal. The material was heated with stirring to a temperature of 190°–215° C. Heating was continued until gas evolution ceased, usually 1–2 hours. The contents were cooled, dissolved in acetone and filtered to remove catalyst. The acetone and newly formed benzylacetone were removed in vacuo and 1.71 g (94%) of crude pregna-4,17(20)-dien-3-one crystallized on standing.

EXAMPLE 2

Example 1 was repeated except that 1% palladium on alumina was used instead of 5% palladium on charcoal. The resulting material had the same assay as Example 1.

EXAMPLE 3

Example 1 was repeated except the benzalacetone was deleted. The resulting material showed the presence of about 25% pregna-4,17(20)-dien-3-one (cis/trans mixture) and 75% pregn-4-en-3-one.

EXAMPLE 4

3-Ketodinor-4-cholen-22-aldehyde (2.0 g, 0.006 mole) and benzalacetone (0.89 g, 0.006 mole) and quinoline (1.0 g, 0.0077 mole) were mixed with 00.1 g of 1% palladium on alumina. The material was heated to a temperature of 245°–260° C. Heating was continued until gas evolution stopped, usually 1–3 hours depending on temperature. The contents were cooled, dissolved in acetone, and filtered to remove catalyst. All volatiles were removed in vacuo and afforded a high yield of the crude pregna-4,17(20)-dien-3-one.

EXAMPLE 5

Example 1 was repeated except that 5% rhodium on carbon was used in place of 5% palladium on carbon. An NMR (Nuclear Magnetic Resonance) assay showed pregna-4,20-dien-3-one and pregna-4,17(20)-dien-3-one.

The process of the present invention provides a method for the dehydroformylation of dinorcholanaldehydes and dinorcholenaldehydes to form 17(20)-pregnenes or 20-pregnenes. These 17(20)-pregnenes or 20-pregnenes can then be used for preparation of valuable steroids such as the corticosteroids.

The invention has been described in detail with particular reference to preferred embodiments thereof, but it will be understood that variations and modifications can be effected within the spirit and scope of the invention.

We claim:

1. A process for dehydroformylating a steroidal aldehyde of the group consisting of dinorcholan-22-aldehydes and dinorcholen-22-aldehydes to the corresponding 17(20)-pregnenes or 20-pregnenes which comprises heating the aldehyde at a temperature of at least 160° C. in the presence of a noble metal catalyst.

2. A process according to claim 1 wherein said catalyst is used in an amount equal to about 3 to 7 percent based on the weight of the aldehyde to be dehydroformylated.

3. A process according to claim 2 wherein said catalyst is palladium on charcoal or alumina.

4. A process according to claim 3 wherein said dehydroformylation is carried out in the presence of at least one hydrogen acceptor selected from the group consisting of benzalacetone, cinnamaldehyde, mesityl oxide, quinoline and benzylideneacetophenone.

5. A process according to claim 4 wherein said hydrogen acceptor is benzalacetone.

6. A process according to claim 4 wherein said hydrogen acceptor is benzalacetone and quinoline.

7. A process according to claim 2 wherein said catalyst is rhodium on charcoal or alumina.

8. A process according to claim 7 wherein said dehydroformylation is carried out in the presence of at least one hydrogen acceptor selected from the group consisting of benzalacetone, cinnamaldehyde, mesityl oxide, quinoline and benzylideneacetophenone.

9. A process according to claim 8 wherein said hydrogen acceptor is benzalacetone.

10. A process according to claim 8 wherein said hydrogen acceptor is benzalacetone and quinoline.

11. A process according to claim 5 wherein said dinorcholen-22-aldehyde is 3-ketodinor-4-cholen-22-aldehyde.

12. A process according to claim 9 wherein said dinorcholen-22-aldehyde is 3-ketodinor-4-cholen-22-aldehyde.

* * * * *